(12) United States Patent
Fedida

(10) Patent No.: US 7,326,239 B1
(45) Date of Patent: Feb. 5, 2008

(54) STRUCTURE OF A PROSTHESIS INTENDED TO BE IMPLANTED IN A HUMAN OR ANIMAL PASSAGE AND PROSTHESIS WITH SUCH A STRUCTURE

(75) Inventor: José Fedida, Chemin des Adrets (FR)

(73) Assignee: Novatech SA, Grasse le Plan (FR)

( * ) Notice: Subject to any disclaimer, the term of this patent is extended or adjusted under 35 U.S.C. 154(b) by 1539 days.

(21) Appl. No.: 09/526,547

(22) Filed: Mar. 16, 2000

(30) Foreign Application Priority Data

Aug. 9, 1999 (FR) .................................. 99 10318

(51) Int. Cl.
*A61F 2/06* (2006.01)
(52) U.S. Cl. ...................................... 623/1.15; 606/108
(58) Field of Classification Search ........ 623/1.1–1.22; 606/108, 191, 194, 195; 608/198
See application file for complete search history.

(56) References Cited

U.S. PATENT DOCUMENTS

| | | | | |
|---|---|---|---|---|
| 5,405,377 A | * | 4/1995 | Cragg | 623/1.2 |
| 5,609,627 A | * | 3/1997 | Goicoechea et al. | 128/898 |
| 5,693,088 A | * | 12/1997 | Lazarus | 623/1.35 |
| 5,873,906 A | | 2/1999 | Lau et al. | |
| 5,984,949 A | * | 11/1999 | Levin | 606/216 |
| 6,197,049 B1 | * | 3/2001 | Shaolian et al. | 623/1.35 |
| 6,211,100 B1 | * | 4/2001 | Legare | 442/36 |
| 6,221,100 B1 | * | 4/2001 | Strecker | 623/1.22 |

FOREIGN PATENT DOCUMENTS

| | | |
|---|---|---|
| EP | 0691108 A1 | 1/1996 |
| EP | 0749729 A2 | 12/1996 |
| EP | 0808612 A1 | 11/1997 |
| EP | 0808614 A2 | 11/1997 |
| EP | 0880948 A1 | 12/1998 |
| FR | 2745172 | 8/1997 |
| FR | 2745172 A1 | 8/1997 |
| WO | 9521592 | 8/1995 |
| WO | WO9521592 | 8/1995 |

* cited by examiner

*Primary Examiner*—Vy Q. Bui
(74) *Attorney, Agent, or Firm*—Stevens, Davis, Miller & Mosher, LLP

(57) ABSTRACT

The present invention relates to a structure of a prosthesis intended to be implanted in a human or animal passage, particularly an artery, to provide through-passage along said passage, said structure (2) comprising at least one mesh (4) which, at least in part, is approximately cylindrical and comprises at least one corrugated filament (F) forming approximately annular units (UA) linked together, at least some of the corrugations (ON) of said corrugated filament (F) of two respective adjacent units (UA) being linked to one another by linking means (5).

According to the invention, at least some of said linking means (5) comprise links (6A, 6C) which are made as a rigid piece and which are provided with at least two loops joined together and, in the case of each of said links (6A, 6C), each of the two loops of the link (6A, 6C) entraps, with some clearance, one of the two corrugations (ON) which are to be linked together.

23 Claims, 3 Drawing Sheets

STRUCTURE OF A PROSTHESIS INTENDED TO BE IMPLANTED IN A HUMAN OR ANIMAL PASSAGE AND PROSTHESIS WITH SUCH A STRUCTURE

The present invention relates to a structure of a prosthesis intended to be implanted in a human or animal passage, and to a prosthesis with such a structure.

Such a prosthesis which, in the context of the present invention, is intended to provide (that is to say to reestablish or to preserve) through-passage along the human or animal passage in which it is implanted, relates more specifically although not exclusively to a simple or bifurcated vascular prosthesis.

It is known that a vascular prosthesis of this type may be used, in particular:

a) to reestablish a sufficiently wide passage for blood along an artery, particularly in the event of stenosis. The prosthesis, which then serves to widen the passage or artery generally has a structure with shape memory which can be brought from a folded position, allowing it to be implanted, into a position in which it is deployed in the artery, so as to widen the latter; or b) to preserve such a passage, particularly when treating an aneurysm. In this case, the prosthesis comprises, in addition to a structure as aforementioned, an impervious outer envelope at least partially surrounding said structure. The prosthesis is implanted in the artery in such a way that this envelope completely covers the aneurysm and therefore serves to transport blood along this weakened part of the artery.

Numerous examples of structures for such prostheses are known. By way of example, mention may be made of documents EP-0 691 108, FR-2 745 172, EP-0 880 948, EP-0 808 614, EP-0 808 612 or WO 95/21592.

Of these documents, document WO-95/21592 in particular describes a structure of a prosthesis which comprises an approximately cylindrical mesh. This mesh consists of a filament which is configured in such a way as to form corrugated rings which are linked together so as to form said cylindrical mesh. For this purpose, at least some of the corrugations of said corrugated filament of two respective adjacent rings, are linked together by linking means. The linking means preferred by this known document are sutures.

Other types of linking means for the same type of structure or for similar structures are also known. These in particular include the following:

welds (document FR-2 745 172);

staples (the aforementioned document WO-95/21592); or an embodiment in which the mesh (filament and linking means) is made in one piece. In this case, the mesh may, in particular, be obtained by cutting material from an item in sheet form (document WO-95/32688).

It is quite obvious that in order to allow the structure to fulfill its various functions, the linking means used have, in particular:

to provide a robust and permanent linkage, since any breakage of such a linkage could have tragic consequences for the patient;

to be extremely supple, both to allow the prosthesis to be implanted and to allow it to function; and not to harm the patient, and in particular not to injure the interior wall of the passage in which the prosthesis is implanted.

However, none of the known linking means is able to satisfy all of these conditions simultaneously. Specifically:

the welds are rigid and are therefore not able to afford the structure the necessary suppleness. Furthermore, when the structure is brought into the folded position with a view to implanting, there is a risk that these welds might at least partially break, thus weakening the structure. Furthermore, if such breakage does occur, the structure may present roughnesses liable to be injurious to the arterial wall;

linkages cut out from material are also too rigid to allow the structure the necessary suppleness. Furthermore, such a structure is complicated to produce; and staples have limited suppleness, particularly given that they firmly grip the filament that is to be linked. Furthermore, the fitting of such a staple is liable to damage the filament.

The object of the present invention is to overcome these drawbacks. This invention relates to a prosthesis structure of the aforementioned type, which is very reliable and very supple, and which can, for example, easily and in complete safety, be brought from a folded position, in which it can be implanted in an artery, into a deployed position of functioning in the artery and which can be kept in this deployed position in complete safety.

To this end, according to the invention, said structure which comprises at least one corrugated filament forming approximately annular units linked together, at least some of the corrugations of said corrugated filament of two respective adjacent units being linked together by linking means, is noteworthy in that at least some of said linking means comprise links which are made as a rigid piece and which are provided with at least two loops joined together and in that, in the case of each of said links, each of the two loops of said link entraps, with some clearance, a respective one of the two corrugations which are to be linked together.

Thus, by virtue of the invention:

as the linking means comprise links which are made as a rigid piece and which comprise loops entrapping the corrugations of the filament, the rigid links cannot break under the pressures liable to be exerted on the structure and the corrugations cannot escape from said loops because the linkage thus obtained is very robust and durable;

as the corrugations are entrapped with a certain amount of clearance in the loops, they can move around easily, thus making the structure very supple. This in particular makes it possible to avoid permanent creases which often exist in known connecting means (welding, etc.) once the structure has been folded between its various possible positions, such permanent creases being liable to reduce the cross-sectional area of the passageway that is to be created using the implanted prosthesis; and as each link has at least two loops, that is to say one loop per corrugation or part of filament to be linked, the parts of filaments thus linked are independent of one another, thus improving the suppleness of the structure, firstly by preventing these parts of filament from rubbing together and secondly by separating from one another the two parts of the structure which are associated one with each of these two parts of filament.

It will be noted that in the context of the present invention, at least some of the links may have more than two loops, which allows more than two corrugations or parts of filaments to be linked together simultaneously. An embodiment such as this may, for example, be of benefit for fixing the links of the structure in the region of bifurcations or in the region of a change of diameter of the cylindrical mesh.

In a preferred first embodiment, at least one of said links comprises at least:
a straight central portion; and
at each of the ends of said central portion, at least one portion in the shape of an arc of a circle intended to form at least part of a loop of the link.

In a second embodiment, at least one of said links comprises at least:
a central portion comprising two straight partial portions which are not aligned and which are connected together; and
at the free end of each of said partial portions, at least one portion in the shape of an arc of a circle intended to form at least part of one loop of the link.

Furthermore, as a preference, at least one of said links has the overall shape of an S, defined in a single plane.

However, this is not the only possible embodiment. Specifically, it is conceivable, within the context of the present invention, that, in the case of at least one of said links, one of the two loops of said link is defined or located in a first plane which differs from a second plane in which the other loop of the link is defined or located.

Furthermore, according to the invention:
in a first alternative form, at least one of the loops of at least one of said links is entirely closed, thus affording an extremely robust attachment; and
in a second alternative form, at least one of the loops of at least one of said links is partially closed so as to be able to entrap the corrugation that is to be linked, which makes the link easier to fit because, during this fitting, it is not necessary to exert force to completely close the loop.

Furthermore, in the context of the present invention, the mesh and, in particular, its openings, may take on different shapes. In particular, advantageously:
in a first embodiment, at least some of said corrugations are zigzags; and
in a second embodiment, said mesh at least partially comprises hexagonal mesh openings so as to obtain a so-called honeycomb shape.

Furthermore, advantageously, at least one of said links is radio-opaque which, in particular, allows the structure according to the invention to be detected and pinpointed easily by radiography while it is being implanted or after it has been implanted in the body of a patient. To improve this detection, said structure advantageously comprises a number of radio-opaque links arranged longitudinally with respect to said cylindrical mesh.

The present invention also relates to a prosthesis intended to be implanted in a human or animal passage to provide through-passage along said passage. According to the invention, said prosthesis, for example a simple tubular prosthesis or a bifurcated prosthesis, has at least one structure such as the aforementioned. Depending on the envisioned applications (treatment of an aneurysm for example), it may also comprise at least one impervious envelope externally and/or internally at least partially surrounding said structure.

Also, as a preference, said impervious envelope has a turned-back region at least at one of the ends of said structure, which makes it possible to obtain a good seal at this end if it is assembled with another prosthesis, for example when assembling legs on the branches of a bifurcated prosthesis.

The figures of the appended drawing will make it easy to understand how the invention may be embodied. In these figures, identical references denote similar elements.

FIG. 1 diagrammatically illustrates part of a structure of a prosthesis according to the invention.

Figure 5:
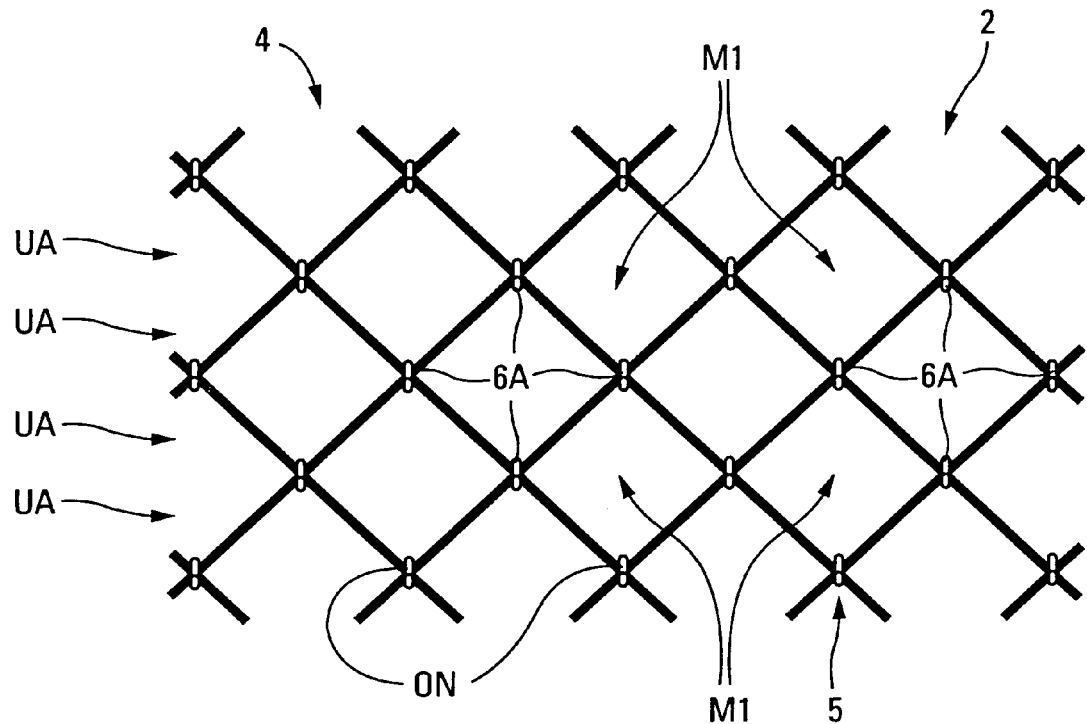
Figure 6:
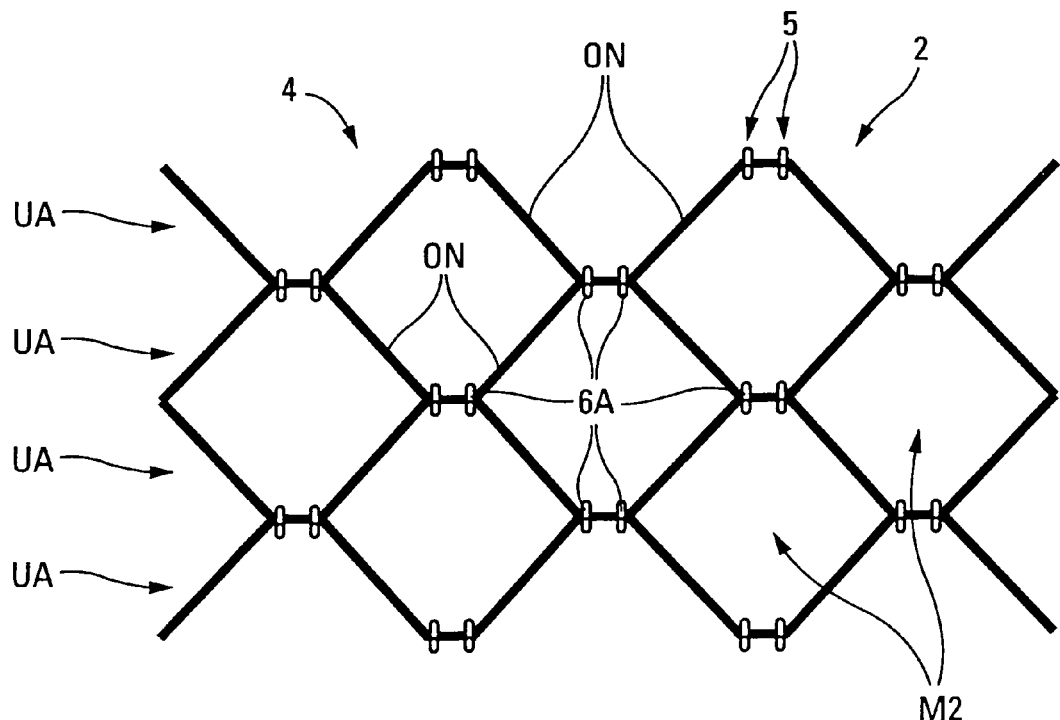

FIGS. 5 and 6 respectively show two embodiments of links of a structure according to the invention.

Figure 7:
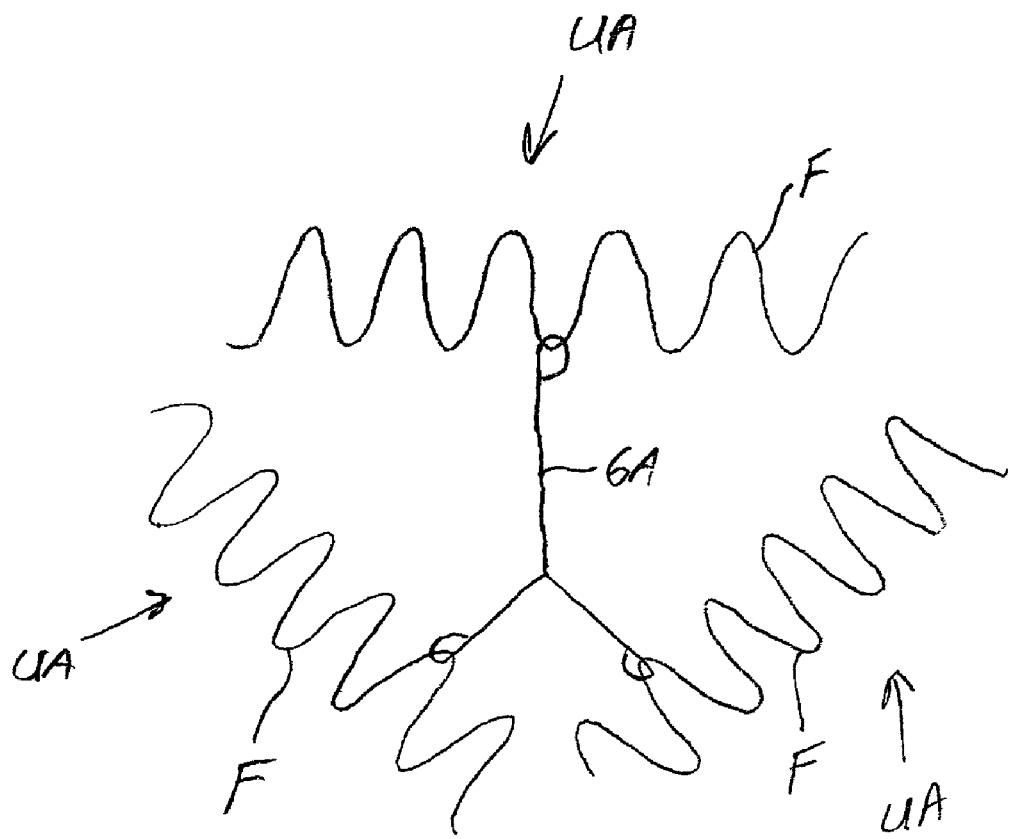

FIG. 7 illustrates a link connecting three mesh structures together according to another embodiment of the invention.

Figure 1:
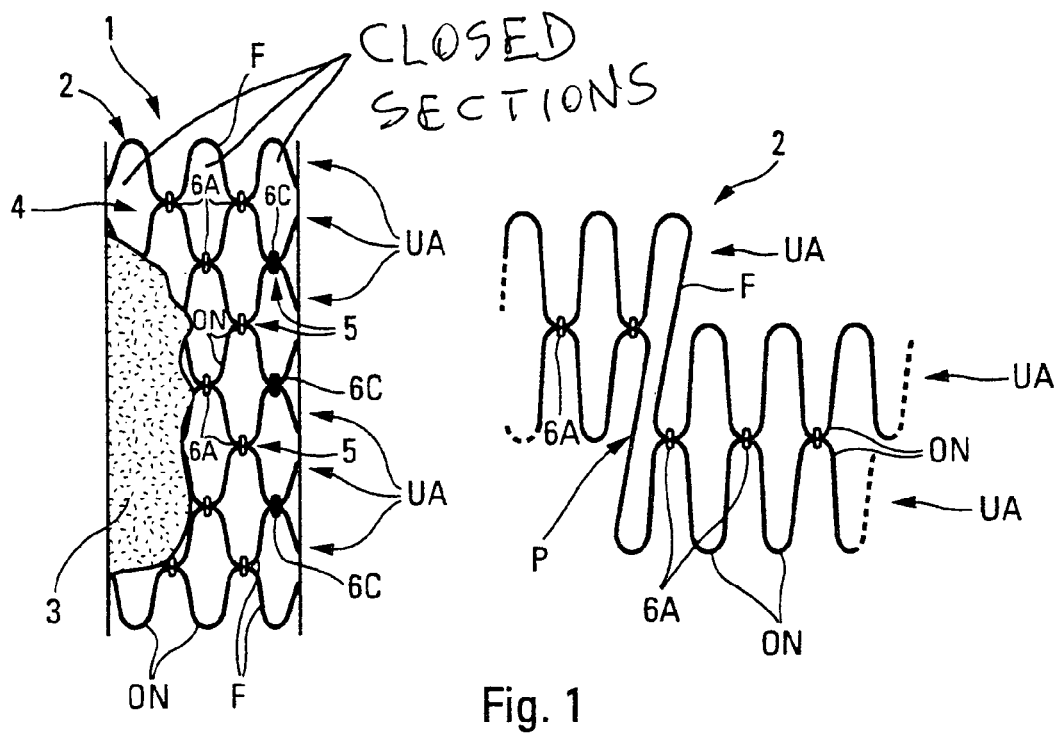

The prosthesis 1 according to the invention and depicted diagrammatically in FIG. 1 is intended to be implanted in a human or animal passage, particularly in an artery, to provide, that is to say to preserve or to reestablish, through-passage along said passage.

Although not exclusively, this prosthesis 1 is more particularly intended to treat physical deficiencies, such as aneurysms or stenoses of arteries in the human body.

To this end, depending on the deficiency being treated, this prosthesis may simply be of tubular shape or may have a more complex shape, for example a bifurcated shape, tailored, in particular, to the shape of the artery in which it is to be implanted.

Such a prosthesis 1 comprises at least one structure 2 according to the invention and specified hereinbelow. It may be equipped with at least one known impervious outer envelope 3 which at least partially covers said structure 2 and which is depicted, with partial cutaway, in FIG. 1. Said envelope may be internal and/or external to the structure.

By way of a preferred but not exclusive application, such a prosthesis 1:
when equipped with an envelope 3, is suitable for treating aneurysms; and
when it has no such envelope, can be used to widen the passage or artery, particularly for the treatment of stenosis.

The structure 2 is made of a biocompatible material with shape memory so that it can be brought from a folded and compact position which allows it to be implanted in the passage concerned, into a deployed position when in place in said passage.

As can be seen in the left-hand part of FIG. 1, said structure 2 comprises, in the known way, at least one mesh 4 which is at least partially cylindrical and which comprises at least one corrugated filament F forming approximately annular corrugated units UA linked together. These corrugated units UA comprise a number of corrugations ON. What is more, at least some of these corrugations ON, each belonging to two adjacent units UA, are linked together by linking means 5, so that said adjacent units UA are linked together and thus form said cylindrical mesh 4.

In the context of the present invention, each annular unit UA may be made of a specific filament F so that before being linked, the various annular units UA are completely independent of one another.

However, it is equally possible to produce all of the annular units UA with one and the same filament F, as depicted partially in the right-hand part of FIG. 1. For this purpose, the filament F is configured in such a way that having created one annular unit UA it passes onto the next annular unit UA, as depicted, for example, at P.

According to the invention, and in particular, to allow a linkage which is robust, supple, durable and not injurious to the wall of the passage in which the prosthesis 1 is implanted, at least some of the linking means 5 comprise links 6A, 6B, 6C according to the present invention and depicted in FIGS. 1 to 6.

Figures 2, 3, 4:
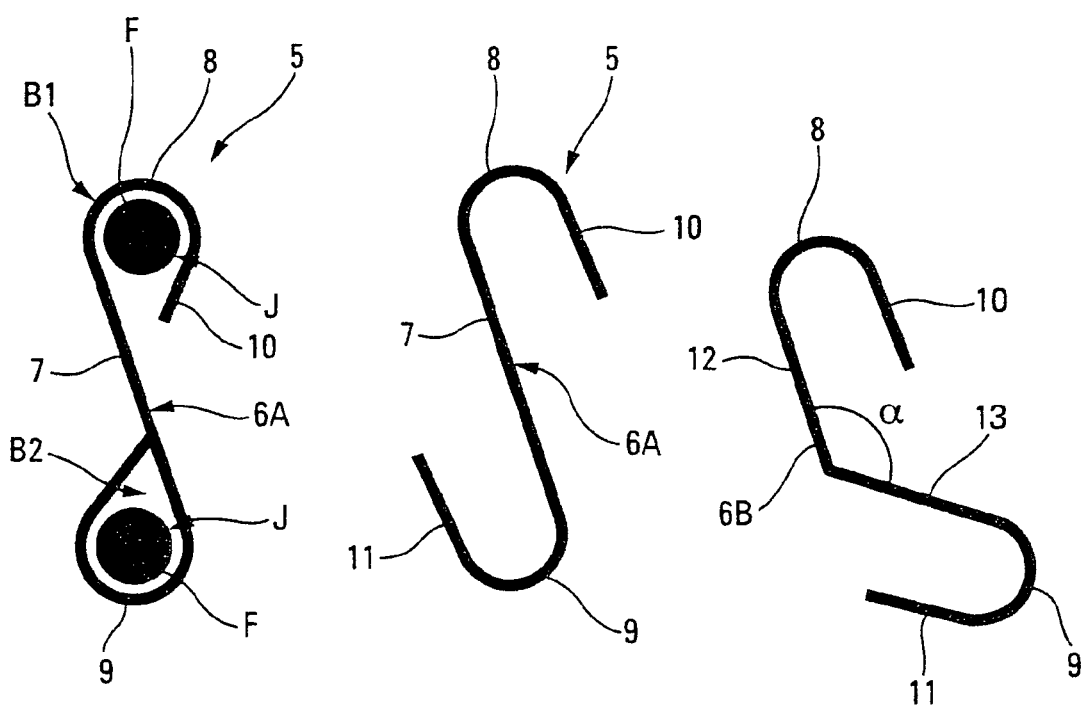
FIGS. 2 and 3 show a first embodiment of a link according to the invention, in a closed position and in an open position, respectively.
FIG. 4 shows a second embodiment of a link according to the invention.

According to the invention, such a link 6A, 6B, 6C is made of a rigid piece and has at least two loops B1 and B2 each of which entraps, with some clearance J, one of the corrugations or parts of filament F that are to be linked together, as can be seen in FIG. 2. The links B1 and B2 are such that the parts of filament (entrapped with clearance) while being joined together can move (turn) freely, thus yielding a link which has the aforementioned characteristics.

Specifically:
- the link is robust and durable, by virtue of the rigidity of the link 6A and the fact that loops B1 and B2 are generated in the actual part of the link 6A;
- the link is very supple, particularly by virtue of the clearance J and the separation between the two parts of filament F which have to be linked together;
- the link does not, for example, have any protruding parts and there is therefore no danger that it will harm the wall of the passage or of the artery in which the prosthesis 1 is to be implanted.

In the context of the present invention, the filament F and the links 6A, 6B and 6C may be made of metal or may, for example be made of a known material marketed under the name of "nitinol".

In a first preferred embodiment depicted in FIGS. 2 and 3, the link 6A comprises:
- a straight central portion 7;
- at each of the ends of said central portion 7, a portion 8, 9 in the shape of an arc of a circle; and
- at each of the ends of said portions 8, 9, a straight end portion 10, 11.

As can be seen in FIGS. 2 and 3, FIG. 2 corresponding to a closed or linking position of the link 6A and FIG. 3 illustrating the open position of this link 6A prior to linking, the portions 8 and 10 and the portions 9 and 11 are curled around the parts of filament F or corrugations, to form the loops B1 and B2 respectively.

In the context of the present invention:
- the loops, such as the loop B2 in FIG. 2, may be completely closed, thus providing an extremely robust connection;
- said loops may also be only partially closed, that is to say just closed up enough to effectively entrap that part of the filament or corrugation that is to be linked, as is the case of the loop B1 in FIG. 2, thus making the loops easier to produce.

The choice between the aforementioned solutions may in particular depend on the properties of the material used to make the link 6A, particularly its rigidity properties.

Of course, the presence of two loops B1 and B2 of different types on the same link 6A is due essentially to reasons of simplifying the drawing. In general, although not exclusively, the loops of one and the same link will actually be of the same type.

In a second embodiment depicted in FIG. 4, the link 6B comprises (rather than a straight central portion 7 as in FIG. 2), at least two straight partial portions 12 and 13 connected together to form an angle α.

This embodiment makes it possible, in particular, to have the loops obtained in the linking position closer together by comparison with the embodiment of FIGS. 2 and 3. This reduction in separation, which is inversely proportional to the size of this (acute) angle α may be beneficial to certain parts of certain types of structure, particularly at the bifurcation of a bifurcated structure.

In this last embodiment, as an alternative, the portions 12 and 13 may be connected together not directly but via at least one additional portion, not depicted.

As a preference, as depicted in FIGS. 2 to 4, the links 6A, 6B according to the invention have the overall shape of an S, defined in a single plane.

However, in another embodiment, not depicted, one of the loops of a link may be defined or located in a first plane which differs from a second plane in which another or the other loop of this link is defined or located.

FIG. 7 illustrates another embodiment of the invention whereby at least some of the links 6A-6C may have more than two loops. This link structure allows more than two corrugations or parts of filaments to be linked together simultaneously. This embodiment may, for example, be of benefit for fixing the links of the structure in the region of bifurcations or in the region of change of diameter of the cylindrical mesh.

Furthermore, to make it possible to detect and thus precisely pinpoint the structure 2 while it is being implanted in a human body or animal or after it has thus been implanted, said structure 2 comprises links 6C according to the invention and illustrated in thick line in FIG. 1, which are radio-opaque and can therefore be detected by radiography. This particular feature may be obtained by the use of an appropriate material or by covering the link 6C with an appropriate coating.

What is more, to allow precise detection of the position of the structure 2, the latter in this case advantageously comprises a number of opaque links 6C located longitudinally with respect to the tubular mesh 4, for example one link per annular unit UA.

In the context of the present invention, the mesh 4 may have mesh openings M1, M2 and corrugations ON of different shapes.

In particular, the corrugations ON may, in particular, be:
- sinusoids, as depicted in FIG. 1; or
- zigzags, as depicted in FIG. 5.

In addition, the mesh openings of the mesh 4 may, in particular, be:
- square in shape, such as the mesh openings M1 depicted in FIG. 5; or
- hexagonal or honeycomb-shaped, such as the mesh openings M2 depicted in FIG. 6.

The invention claimed is:

1. A structure of a prosthesis intended to be implanted in a human or animal passage to provide through-passage along said passage, said structure comprising:
   at least one mesh which, at least in part, is approximately cylindrical and comprises at least one corrugated filament forming approximately annular units linked together, at least some corrugations of said corrugated filament of two respective adjacent units of said annular units being linked together by a plurality of linking means, wherein at least some of said linking means comprise links which are made as a rigid piece,
   wherein each of said links is provided with a sole central portion and two loops, one loop at each of the ends of said central portion,
   wherein each of said two loops allows (a) a first shape of an arc of a circle prior to linking and (b) a second shape of an entirely closed loop, in the linking position,
   wherein each of the two closed loops of each of said links entraps, in said linking position, with some clearance, a respective one of two of said corrugations, which are to be linked together.

2. The structure as claimed in claim 1, wherein each central portion of a link is a straight central portion.

3. The structure as claimed in claim 1, wherein each central portion of a link comprises two straight partial portions which are not aligned and which are connected together to form an acute angle.

4. The structure as claimed in claim 1, wherein, in the case of at least one of said links, one of the two loops is defined in a first plane which differs from a second plane in which the other of the two loops is defined.

5. The structure as claimed in claim 1, wherein at least some of said corrugations are zigzags.

6. The structure as claimed in claim 1, wherein said mesh at least partially comprises hexagonal mesh openings.

7. The structure as claimed in claim 1, wherein at least one of said links is radio-opaque.

8. The structure as claimed in claim 7 wherein said links comprise a number of radio-opaque links arranged longitudinally with respect to said cylindrical mesh.

9. A prosthesis intended to be implanted in a human or animal passage to provide through-passage along said passage, and which comprises at least one structure as specified in claim 1.

10. The prosthesis as claimed in claim 9, and additionally comprising at least one impervious envelope at least partially surrounding said structure.

11. The prosthesis as claimed in claim 10, wherein said impervious envelope has a turned-back region at least at one of the ends of said structure.

12. A structure of a prosthesis intended to be implanted in a human or animal passage to provide through-passage along said passage, said structure comprising:
   at least one mesh which, at least in part, is approximately cylindrical and comprises at least one corrugated filament forming approximately annular units linked together, at least some of the corrugations of said corrugated filament of two respective adjacent units of said annular units being linked together by a plurality of linking means, wherein at least some of said linking means comprise links which are made as a rigid piece,
   wherein each of said links is provided with (a) a single central portion, and (b) two loops comprising one loop at each of the ends of said central portion, wherein each of said two loops allows a first shape of an arc of a circle prior to linking and a second shape of a partially closed loop that is just closed up to entrap the corrugation that is to be linked, in the linking position, and
   wherein each of the two loops of each of said links entraps, in said linking position, with a clearance, a respective one of two of said corrugations, which are to be linked together.

13. The structure as claimed in claim 12, wherein each central portion of a link is a straight central portion.

14. The structure as claimed in claim 12, wherein each central portion of a link comprises two straight partial portions which are not aligned and which are connected together to form an acute angle.

15. The structure as claimed in claim 12, wherein, in the case of at least one of said links, one of the two loops is defined in a first plane which differs from a second plane in which the other of the two loops is defined.

16. The structure as claimed in claim 12, wherein at least some of said corrugations are zigzags.

17. The structure as claimed in claim 12, wherein said mesh at least partially comprises hexagonal mesh openings.

18. The structure as claimed in claim 12, wherein at least one of said links is radio-opaque.

19. The structure as claimed in claim 18 wherein said links comprise a number of radio-opaque links arranged longitudinally with respect to said cylindrical mesh.

20. A prosthesis intended to be implanted in a human or animal passage to provide through-passage along said passage, and which comprises at least one structure as specified in claim 12.

21. The prosthesis as claimed in claim 20, and additionally comprising at least one impervious envelope at least partially surrounding said structure.

22. The prosthesis as claimed in claim 21, wherein said impervious envelope has a turned-back region at least at one of the ends of said structure.

23. A structure of a prosthesis intended to be implanted in a human or animal passage to provide through-passage along said passage, said structure comprising:
   at least one mesh which, at least in part, is approximately cylindrical and comprises at least one corrugated filament forming approximately annular units linked together, at least some corrugations of said corrugated filament of two respective adjacent units of said annular units being linked together by a plurality of linking means, wherein at least some of said linking means comprise links which are made as a rigid piece,
   wherein each of said links is provided with (a) a single central portion, and (b) more than two loops which are connected to said central portion, wherein each of said loops allows a first shape of an arc of a circle prior to linking and a second shape of a closed loop in the linking position, and
   wherein each of the two loops of each of said links entraps, in said linking position, with a clearance, a respective one of two of said corrugations, which are to be linked together.

* * * * *